US012090153B2

(12) United States Patent
Hergenrother et al.

(10) Patent No.: US 12,090,153 B2
(45) Date of Patent: Sep. 17, 2024

(54) COMBINATION THERAPY FOR THE TREATMENT OF UVEAL MELANOMA

(71) Applicant: The Board of Trustees of the University of Illinois, Urbana, IL (US)

(72) Inventors: Paul J. Hergenrother, Champaign, IL (US); Matthew Wesley Boudreau, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 721 days.

(21) Appl. No.: 17/281,453

(22) PCT Filed: Oct. 3, 2019

(86) PCT No.: PCT/US2019/054500
§ 371 (c)(1),
(2) Date: Mar. 30, 2021

(87) PCT Pub. No.: WO2020/072774
PCT Pub. Date: Apr. 9, 2020

(65) Prior Publication Data
US 2022/0000862 A1        Jan. 6, 2022

Related U.S. Application Data

(60) Provisional application No. 62/742,063, filed on Oct. 5, 2018.

(51) Int. Cl.
*A61K 31/496*        (2006.01)
*A61K 9/20*          (2006.01)
(Continued)

(52) U.S. Cl.
CPC .................................. *A61K 31/496* (2013.01)

(58) Field of Classification Search
CPC .... A61K 31/496; A61K 9/2018; A61K 45/06; A61K 31/495; A61K 31/519;
(Continued)

(56) References Cited

U.S. PATENT DOCUMENTS 5,723,459 A    3/1998   Armistead et al.
5,844,001 A    12/1998  McClay et al.
(Continued)

FOREIGN PATENT DOCUMENTS

CA    2866021 A1    9/2013
CN    101184491 A   5/2008
(Continued)

OTHER PUBLICATIONS

Ardini E et al. Entrectinib, a Pan-TRK, ROS1, and ALK Inhibitor with Activity in Multiple Molecularly Defined Cancer Indications. Mol Cancer Ther. Apr. 2016;15(4):628-39. doi: 10.1158/1535-7163. MCT-15-0758. Epub Mar. 3, 2016. PMID: 26939704. (Year: 2016).*
(Continued)

*Primary Examiner* — Deepak R Rao
*Assistant Examiner* — Kevin S Martin
(74) *Attorney, Agent, or Firm* — Haukaas Fortius PLLC; Michael Haukaas

(57) ABSTRACT

Synergistic drug combinations with the small molecule PAC-1 against uveal or cutaneous melanoma. There are no current targeted drug treatments for the mutations associated with uveal melanoma. Despite primary radiation or surgical therapy, up to 50% of patients eventually develop metastatic disease, for which there is no standard therapy nor treatment shown to improve overall survival. Drug combinations with PAC-1 allow the use of lower dosages of this compound that result in cancer cell death in uveal melanoma. Drug combinations of PAC-1 with the kinase inhibitor entrectinib have shown a synergistic effect against uveal melanoma cell lines.

(Continued)

Specifically, PAC-1 and entrectinib are synergistic against wild-type and mutant uveal melanoma cell lines (e.g., GNAQ and GNA11).

21 Claims, 13 Drawing Sheets

(51) Int. Cl.
    *A61K 31/495*     (2006.01)
    *A61K 31/519*     (2006.01)
    *A61K 45/06*     (2006.01)
    *A61P 27/02*     (2006.01)
    *A61P 35/00*     (2006.01)
    *A61P 35/04*     (2006.01)

(58) Field of Classification Search
    CPC ...... A61K 2300/00; A61P 27/02; A61P 35/00; A61P 35/04
    See application file for complete search history.

(56) References Cited

U.S. PATENT DOCUMENTS

| | | |
|---|---|---|
| 6,251,967 B1 | 6/2001 | Perichaud et al. |
| 6,303,329 B1 | 10/2001 | Heinrikson et al. |
| 6,403,765 B1 | 6/2002 | Alnemri |
| 6,534,267 B1 | 3/2003 | Wang et al. |
| 6,762,045 B2 | 7/2004 | Krebs et al. |
| 6,878,743 B2 | 4/2005 | Choong et al. |
| 7,041,784 B2 | 5/2006 | Wang et al. |
| 7,632,972 B2 | 12/2009 | Hergenrother et al. |
| 8,299,057 B2 | 10/2012 | Borgia et al. |
| 8,592,584 B2 | 11/2013 | Hergenrother et al. |
| 8,778,945 B2 | 7/2014 | Hergenrother et al. |
| 8,916,705 B2 | 12/2014 | Hergenrother |
| 9,102,661 B2 | 8/2015 | Hergenrother et al. |
| 9,249,116 B2 | 2/2016 | Chen et al. |
| 9,399,035 B2 * | 7/2016 | Hergenrother ......... A61K 33/24 |
| 9,421,202 B2 | 8/2016 | Hergenrother et al. |
| 9,522,901 B2 | 12/2016 | Hergenrother et al. |
| 9,592,229 B2 | 3/2017 | Hergenrother et al. |
| 9,643,960 B2 | 5/2017 | Hergenrother et al. |
| 9,663,482 B2 | 5/2017 | Hergenrother et al. |
| 10,350,207 B2 | 7/2019 | Hergenrother et al. |
| 11,129,830 B2 | 9/2021 | Hergenrother et al. |
| 11,510,919 B2 * | 11/2022 | Hergenrother ....... A61K 31/519 |
| 2003/0008015 A1 | 1/2003 | Levisage et al. |
| 2004/0077542 A1 | 4/2004 | Wang et al. |
| 2004/0180828 A1 | 9/2004 | Shi |
| 2007/0049602 A1 | 3/2007 | Hergenrother et al. |
| 2009/0010927 A1 | 1/2009 | Yaffe et al. |
| 2010/0291214 A1 | 11/2010 | Gabriele et al. |
| 2011/0031939 A1 | 2/2011 | Funaba et al. |
| 2011/0257398 A1 | 10/2011 | Hergenrother et al. |
| 2012/0040995 A1 | 2/2012 | Hergenrother et al. |
| 2012/0077834 A1 | 3/2012 | Castro et al. |
| 2012/0178803 A1 | 7/2012 | Harn et al. |
| 2014/0348819 A1 | 11/2014 | Golub et al. |
| 2015/0017264 A1 | 1/2015 | Hergenrother et al. |
| 2015/0231132 A1 | 8/2015 | Hergenrother |
| 2016/0346277 A1 | 12/2016 | Hergenrother et al. |
| 2017/0042886 A1 | 2/2017 | Hergenrother et al. |
| 2017/0105989 A1 | 4/2017 | Hergenrother et al. |

FOREIGN PATENT DOCUMENTS

| | | |
|---|---|---|
| CN | 104507479 A | 4/2015 |
| CN | 108135896 A | 6/2018 |
| JP | 2007513962 A | 5/2007 |
| JP | 2008545718 A | 12/2008 |
| JP | 2012526824 A | 11/2012 |
| JP | 2015509965 A | 4/2015 |
| JP | 2018516936 A | 6/2018 |
| RU | 2360692 C1 | 7/2009 |
| RU | 2408584 C2 | 1/2011 |
| RU | 2410389 C2 | 1/2011 |
| RU | 2438695 C2 | 1/2012 |
| WO | 2006128173 A2 | 11/2006 |
| WO | 2007033374 A2 | 3/2007 |
| WO | 2007137200 A2 | 11/2007 |
| WO | 2008134474 A3 | 1/2009 |
| WO | 2009089508 A1 | 7/2009 |
| WO | 2010091382 A1 | 8/2010 |
| WO | 2010091383 A2 | 8/2010 |
| WO | 2010132440 A2 | 11/2010 |
| WO | 2010138141 A1 | 12/2010 |
| WO | 2010151746 A2 | 12/2010 |
| WO | 2012118978 A1 | 9/2012 |
| WO | 2013014448 A1 | 1/2013 |
| WO | 2013134398 A1 | 9/2013 |
| WO | 2013134407 A2 | 9/2013 |
| WO | 2013134407 A3 | 9/2013 |
| WO | 2014072357 A1 | 5/2014 |
| WO | 2014138279 A1 | 9/2014 |
| WO | 2014193898 A1 | 12/2014 |
| WO | 2015004636 A1 | 1/2015 |
| WO | WO-2016197129 A1 * | 12/2016 ......... A61K 31/4184 |
| WO | 2017106492 A1 | 6/2017 |
| WO | WO-2018106595 A1 * | 6/2018 .......... A61K 31/444 |
| WO | 2018170381 A1 | 9/2018 |

OTHER PUBLICATIONS

Chattopadhyay C, Kim DW, Gombos DS, Oba J, Qin Y, Williams MD, Esmaeli B, Grimm EA, Wargo JA, Woodman SE, Patel SP. Uveal melanoma: From diagnosis to treatment and the science in between. Cancer. Aug. 1, 2016;122(15):2299-312. doi: 10.1002/cncr.29727. Epub Mar. 15, 2016. PMID: 26991400; PMCID: PMC5567680. (Year: 2016).*

Soria JC et al. Osimertinib in Untreated EGFR-Mutated Advanced Non-Small-Cell Lung Cancer. N Engl J Med. Jan. 11, 2018;378(2): 113-125. doi: 10.1056/NEJMoa1713137. Epub Nov. 18, 2017. PMID: 29151359. (Year: 2018).*

Dasgupta B, Seibel W. Compound C/Dorsomorphin: Its Use and Misuse as an AMPK Inhibitor. Methods Mol Biol. 2018; 1732: 195-202. doi: 10.1007/978-1-4939-7598-3_12. PMID: 29480476. (Year: 2018).*

Cross et al., "AZD9291, an Irreversible EGFR TKI, Overcomes T790M-Mediated Resistance to EGFR Inhibitors in Lung Cancer," Cancer Discov., 4(9):1046-1061, Sep. 2014.

Extended Search Report of the European Patent Office dated Dec. 13, 2021in EP Application No. 18879684.1; 16pgs.

Hrustanovic et al., "RAS-MAPK Dependence Underlies a Rational Polytherapy Strategy in EML4-ALK-Positive Lung Cancer," Nat Med., 21(9):1038-10347, Sep. 2015.

"Melanoma: Catching and Curing Skin Cancer—Research Summary," accessed on the internet at https://www.theeagle.com/archives/melanoma-catching-and-curing-skin-cancer---researchsummary/article_85ae6fdb-034f-5921-89be-57d5aeeeb0be.html, retrieved Jun. 8, 2020, 3pgs.

Ardini et al., "Entrectinib, a Pan-TRK, ROS1, and ALK Inhibitor with Activity in Multiple Molecularly Defined Cancer Indications," Mol Cancer Ther., 15(4):628-639, Apr. 2016.

Atefi et al., "Reversing Melanoma Cross-Resistance to BRAF and MEK Inhibitors by Co-Targeting the AKT/mTOR Pathway," PLoS One., 6(12):e28973, Dec. 2011.

Aveic et al., "Combating Autophagy Is a Strategy to Increase Cytotoxic Effects of Novel ALK Inhibitor Entrectinib in Neuroblastoma Cells," Oncotarget, 7(5):5646-5563, Feb. 2016.

Botham et al., "Small-Molecule Procaspase-3 Activation Sensitizes Cancer to Treatment with Diverse Chemotherapeutics," ACS Cent Sci., 2(8):545-559, Aug. 2016.

Botham et al., "Small-Molecule Procaspase-3 Activation Sensitizes Cancer to Treatment with Diverse Chemotherapeutics," ACS Cent Sci., 2(8):545-559, Aug. 2016, Supporting Information.

(56) References Cited

OTHER PUBLICATIONS

Boudreau et al., "Procaspase-3 Overexpression in Cancer: A Paradoxical Observation with Therapeutic Potential," ACS Chem. Biol., 14(11):2335-2348, Jul. 2019.
Broecker-Preuss et al., "Sorafenib Inhibits Intracellular Signaling Pathways and Induces Cell Cycle Arrest and Cell Death in Thyroid Carcinoma Cells Irrespective of Histological Origin or BRAF Mutational Status," BMC Cancer, 15(1):184, Dec. 2015.
Buder et al., "Systemic Treatment of Metastatic Uveal Melanoma: Review of Literature and Future Perspectives," Cancer Med., 2(5):674-686, Oct. 2013.
Cai et al., "Tamoxifen Inhibits Nitrobenzylthioinosine-Sensitive Equilibrative Uridine Transport in Human MCF-7 Breast Cancer Cells," Biochem J., 320(Pt 3):991-995, Dec. 1996.
CAPLUS, Procaspase, Jun. 2015, 7pgs.
CAPLUS, Temozolomide (L) Procaspase-1, Apr. 2016, 1pg.
Chen et al., "Caspases and Inhibitor of Apoptosis Proteins in Cutaneous and Mucosal Melanoma: Expression Profile and Clinicopathologic Significance," Hum Pathol., 40(7):950-956, Jul. 2009.
Chen et al., "Signaling Pathways and Potential Molecular Targets in Uveal Melanoma," Retrieved from the Internet at https://smjournals.com/ebooks/management-of-malignant-melanoma/chapters/, Jul. 2017.
Das Thakur et al., "Modelling Vemurafenib Resistance in Melanoma Reveals a Strategy to Forestall Drug Resistance," Nature, 494(7436):251-255, Feb. 2013.
Dawson James Securities, Institutional Research: Health Care and Technology Industry Note, "Comparative Oncology: A New 'Breed' of Trial Set to Improve Clinical Success in Oncology," Dec. 8, 2015, 19pgs.
Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)," Cancer Discov., 7(4):400-409, Apr. 2017.
Extended Search Report of the EPO dated Nov. 20, 2017 in EP Application No. 17180400.8; 5pgs.
Extended Search Report of the EPO dated Sep. 24, 2015 in EP Application No. 13758061.9; 5pgs.
Feng et al., "A Platform of Synthetic Lethal Gene Interaction Networks Reveals that the GNAQ Uveal Melanoma Oncogene Controls the Hippo Pathway through FAK," Cancer Cell, 35(3):457-472, Mar. 2019.
Golub et al., "Molecular Classification of Cancer: Class Discovery and Class Prediction by Gene Expression Monitoring," Science, 286(5439):531-537, Oct. 1999.
Ho et al., "Acquired BRAF V600E Mutation as Resistant Mechanism after Treatment with Osimertinib," J Thorac Oncol., 12(3):567-572, Mar. 2017.
Huang et al., "Predicting Drug Combination Index and Simulating the Network-Regulation Dynamics by Mathematical Modeling of Drug-Targeted EGFR-ERK Signaling Pathway," Sci. Rep., 7:40752, Jan. 2017.
International Preliminary Report on Patentability for PCT/US2013/029391 dated Sep. 18, 2014, 5pgs.
International Preliminary Report on Patentability for PCT/US2013/029405 dated Sep. 18, 2014, 7pgs.
International Search Report and Written Opinion of the ISA/RU in PCT/US2013/029391 dated Jun. 14, 2013; 2pgs.
International Search Report and Written Opinion of the ISA/RU in PCT/US2013/029405, dated Aug. 15, 2013; 9pgs.
International Search Report and Written Opinion of the ISA/US in PCT/US2016/036063, dated Sep. 14, 2016; 15pgs.
International Search Report and Written Opinion of the ISA/US in PCT/US2018/061579, dated Feb. 1, 2019; 9pgs.
International Search Report and Written Opinion of the ISA/US in PCT/US2019/054500, dated Dec. 18, 2019; 12pgs.
Joseph et al., "The RAF Inhibitor PLX4032 Inhibits ERK Signaling and Tumor Cell Proliferation in a V600E BRAF-Selective Manner," Proc Natl Acad Sci U S A., 107(33):14903-14908, Aug. 2010.
Kaliki et al., "Uveal Melanoma: Relatively Rare but Deadly Cancer," Eye (Lond)., 31(2):241-257, Feb. 2017.
Kfoury et al., "AMPK Promotes Survival of C-Myc-Positive Melanoma Cells by Suppressing Oxidative Stress," EMBO J., 37(5):e97673, Mar. 2018.
Larkin et al., "Combined Vemurafenib and Cobimetinib in BRAF-Mutated Melanoma," N Engl J Med., 371(20):1867-1876, Nov. 2014.
Lori et al., "Doxorubicin and Cyclophosphamide for the Treatment of Canine Lymphoma: A Randomized, Placebo-controlled Study," Vet Comp Oncol., 8(3):188-195., Sep. 2010.
Lu et al., "Cetuximab Reverses the Warburg Effect by Inhibiting HIF-1—Regulated LDH-A," Mol Cancer Ther., 12 (10):2187-2199, Oct. 2013.
Luke et al., "Biology of Advanced Uveal Melanoma and Next Steps for Clinical Therapeutics," Pigm Cell Melanoma Res., 28(2):135-147, Mar. 2015.
Martin et al., "Concurrent MEK and Autophagy Inhibition Is Required to Restore Cell Death Associated Danger-Signalling in Vemurafenib-Resistant Melanoma Cells," Biochem Pharmacol., 93(3):290-304, Feb. 2015.
Medline, "Cancer," accessed on the internet at http://www.nlm.nih.gov/medlineplus/cancer; retrieved Mar. 19, 2017; 14pgs.
Menichincheri et al., "Discovery of Entrectinib: A New 3-Aminoindazole As a Potent Anaplastic Lymphoma Kinase (ALK), c-ros Oncogene 1 Kinase (ROS1), and Pan-Tropomyosin Receptor Kinases (Pan-TRKs) inhibitor," J Med Chem., 59(7):3392-3408, Apr. 2016.
Patel et al., "Expression of Executioner Procaspases and Their Activation by a Procaspase-Activating Compound in Chronic Lymphocytic Leukemia Cells," Blood, 125(7):1126-1136, Feb. 2015.
Patel et al., "Therapeutic Implications of the Emerging Molecular Biology of Uveal Melanoma," Clin Cancer Res., 17(8):2087-2100, Apr. 2011.
Peh et al., "Overcoming Resistance to Targeted Anticancer Therapies through Small-Molecule-Mediated MEK Degradation," Cell Chem Biol., 25(8):996-1005, Aug. 2018.
Peh et al., "The Combination of Vemurafenib and Procaspase-3 Activation Is Synergistic in Mutant BRAF Melanomas," Mol Cancer Ther., 15(8):1859-1869, Aug. 2016.
Peng et al. "The Inhibition of PAC-1,L-OHP and PAC-1 plus L-OHP on the Human Colorectal Cancer Cell" Zhongguo Putong Waike Zazhi, 19(10):1097-1102, Oct. 2010.
Peterson et al., "Discovery and Canine Preclinical Assessment of a Nontoxic Procaspase-3-Activating Compound," Cancer Research, 70:7232-7241, Sep. 2010.
Peterson et al., "PAC-1 Activates Procaspase-3 in Vitro through Relief of Zinc-Mediated Inhibition," J. Mol. Biol., 388:144-158, Mar. 2009.
Peterson et al., "Procaspase-3 Activation as an Anti-Cancer Strategy: Structure—Activity Relationship of Procaspase-Activating Compound 1 (PAC-1) and Its Cellular Co-Localization with Caspase-3," J. Med. Chem.,59:5721-5731, Aug. 2009.
Putt et al., "Small-Molecule Activation of Procaspase-3 to Caspase-3 as a Personalized Anticancer Strategy," Nat. Chem. Biol., 2(10):543-550, Aug. 2006.
Rasheed et al., "Cyclodextrins as Drug Carrier Molecule: A Review.," Sci Pharm., 76(4):567-598, Nov. 2008.
Partial Search Report of the European Patent Office dated Aug. 9, 2021 in EP Application No. 18879684.1; 15pgs.
Razi et al. "Paclitaxel Cytotoxicity is Significantly Enhanced by a Novel Pro-apoptotic Agent in the Treatment of Non-small Cell Lung Cancer." J. American College of Surgeons, 213(3) Suppl 1, pp. S42, Sep. 2011.
Robert et al., "Improved Overall Survival in Melanoma with Combined Dabrafenib and Trametinib," N Engl J Med, 372(1):30-39, Jan. 2015.
Rowe et al., "Handbook of Pharmaceutical Excipients," 5th Ed.; Royal Pharmaceutical Society of Great Britain; pp. 217-221; 2006.
Ryu et al., "Therapeutic Inhibitors against Mutated BRAF and MEK for the Treatment of Metastatic Melanoma," Chonnam Med J., 53(3):173-177, Sep. 2017.

(56) References Cited

OTHER PUBLICATIONS

Smith, Cancer Treatment from a Vet, accessed on the internet at http://blogs.www.redorbit.com/author/smith, retrieved Feb. 28, 2015, 3pgs.

STN CAS RN 1103440 60 3 entered Feb. 9, 2009.

Sweetlove et al., "Inhibitors of Pan-PI3K Signaling Synergize with BRAF or MEK Inhibitors to Prevent BRAF-Mutant Melanoma Cell Growth," Front Oncol., 5(135): 1-14, Jun. 2015.

Temozoloamide Product Specification, accessed on the internet at http://www.cancer.gov/cancertopics/druginfo/temozolomide/print, downloaded Mar. 25, 2015, 2pgs, Oct. 2006.

Wang et al. "A Novel Small-Molecule Activator of Procaspase-3 Induces Apoptosis in Cancer Cells and Reduces Tumor Growth in Human Breast, Liver and Gallbladder Cancer Xenografts," Mol Oncol., 8(8):1640-1652, Dec. 2014.

Wolan et al., "Small-Molecule Activators of a Proenzyme," Science, 326(5954):853-858, Nov. 2009.

Yang et al., "The p53-dependent Apoptotic Pathway of Breast Cancer Cells (BC-MI) Induced by the bis-type Bioreductive Compound Aziridinylnaphthoquinone," Breast Cancer Res., 7(1):RI9-R27, Epub Nov. 4, 2004.

Zheng et al., "Inhibitory Effect of of Pyrvinium Pamoate on Uveal Melanoma Cells Involves Blocking of Wnt/β-Catenin Pathyway," Acta Biochim Biophys Sin (Shanghai)., 49(10):890-898, Oct. 2017.

Zorn et al., "Self-Assembling Small Molecules Form Nanofibrils That Bind Procaspase-3 To Promote Activation," J Am Chem Soc., 133(49):19630-19633, Nov. 2011.

Extended Search Report and Written Opinion of the European Patent Office dated May 11, 2022 in EP Application No. 19869986.0 (EP3852744); 9pgs.

Boudreau et al., "The combination of PAC-1 and entrectinib for the treatment of metastatic uveal melanoma," Melanoma Res., 33(6):514-524, Dec. 2023.

Wang et al., "The development and progress of ALK inhibitors", Chinese Journal of Medical Frontiers, vol. 10, No. 7, pp. 44-49, Jul. 2018.

* cited by examiner

MEL 270$^{Gq}$

PAC-1/μM

| | 0 | 1 | 2 | 3 | 4 | 5 |
|---|---|---|---|---|---|---|
| 0 | 0 ± 0 | -3 ± 8 | 10 ± 4 | 14 ± 1 | 24 ± 6 | 29 ± 3 |
| 0.0625 | 10 ± 2 | 13 ± 4 | 23 ± 4 | 26 ± 1 | 39 ± 2 | 38 ± 3 |
| 0.125 | 13 ± 1 | 15 ± 4 | 26 ± 1 | 31 ± 3 | 42 ± 2 | 49 ± 2 |
| 0.25 | 16 ± 2 | 18 ± 4 | 32 ± 3 | 38 ± 2 | 49 ± 4 | 59 ± 3 |
| 0.5 | 18 ± 2 | 23 ± 2 | 41 ± 3 | 54 ± 2 | 64 ± 5 | 74 ± 4 |
| 0.625 | 16 ± 2 | 27 ± 5 | 40 ± 2 | 61 ± 2 | 67 ± 3 | 79 ± 3 |
| 1 | 23 ± 1 | 35 ± 3 | 62 ± 4 | 71 ± 3 | 81 ± 3 | 86 ± 3 |
| 1.25 | 22 ± 4 | 40 ± 4 | 59 ± 3 | 75 ± 1 | 85 ± 3 | 88 ± 1 |
| 2.5 | 30 ± 2 | 54 ± 4 | 70 ± 3 | 83 ± 2 | 87 ± 2 | 90 ± 1 |
| 5 | 62 ± 1 | 78 ± 2 | 88 ± 1 | 95 ± 1 | 96 ± 0 | 97 ± 0 |
| 10 | 89 ± 1 | 94 ± 1 | 97 ± 0 | 99 ± 0 | 100 ± 0 | 99 ± 0 |

| | 0 | 1 | 2 | 3 | 4 | 5 |
|---|---|---|---|---|---|---|
| 0 | ∞ | ∞ | ∞ | ∞ | ∞ | ∞ |
| 0.0625 | ∞ | 0.68 | 0.60 | 0.75 | 0.63 | 0.80 |
| 0.125 | ∞ | 0.81 | 0.62 | 0.69 | 0.61 | 0.60 |
| 0.25 | ∞ | 0.98 | 0.60 | 0.62 | 0.53 | 0.48 |
| 0.5 | ∞ | 1.13 | 0.55 | 0.43 | 0.37 | 0.31 |
| 0.625 | ∞ | 1.03 | 0.65 | 0.35 | 0.35 | 0.26 |
| 1 | ∞ | 0.94 | 0.32 | 0.27 | 0.21 | 0.19 |
| 1.25 | ∞ | 0.87 | 0.42 | 0.25 | 0.20 | 0.17 |
| 2.5 | ∞ | 0.76 | 0.38 | 0.20 | 0.18 | 0.16 |
| 5 | ∞ | 0.33 | 0.16 | 0.07 | 0.07 | 0.07 |
| 10 | ∞ | 0.09 | 0.05 | 0.02 | 0.00 | 0.03 |

Combination Index = 0  Combination Index ≥ 2

C.

| CI < 1 | CI = 1 | CI > 1 |
|---|---|---|
| Synergistic | Additive | Antagonistic |

| <0.1 | Very Strong Synergism |
|---|---|
| 0.1-0.3 | Strong Synergism |
| 0.3-0.7 | Synergism |
| 0.7-0.9 | Moderate Synergism |
| 0.9-1.1 | Additive |
| 1.1-1.5 | Moderate Antagonism |
| 1.5-2 | Antagonism |
| >2 | Strong Antagonism |

*Fig. 6 (cont'd)*

COMBINATION THERAPY FOR THE TREATMENT OF UVEAL MELANOMA

RELATED APPLICATIONS

This application is a National Stage filing under 35 U.S.C. § 371 of International Application No. PCT/US2019/054500 filed Oct. 3, 2019, which claims priority under 35 U.S.C. § 119(e) to U.S. Provisional Patent Application No. 62/742,063, filed Oct. 5, 2018, which applications are incorporated herein by reference.

GOVERNMENT SUPPORT

This invention was made with government support under Grant No. R01-CA120439 awarded by the National Institutes of Health. The government has certain rights in the invention.

BACKGROUND OF THE INVENTION

Uveal melanoma (UM) is the most common form of ocular melanoma. Approximately 97% of UM patients have an activating mutation in GNAQ/11, triggering constitutive activation of GNAQ/11 signaling and driving UM phenotype. While the cellular biology of UM has been studied extensively in the literature, this breadth of knowledge has not directly translated into better treatments and outcomes for UM patients. While primary UM tumors are typically manageable with a combination of radiation and surgery, 51% of UM patients will exhibit metastatic lesions within 1-5 years. Metastatic uveal melanoma (MUM) is a highly aggressive cancer that typically presents in the liver and is associated with an overall 1-year survival rate of less than 15%.

Current work in the field is focused on utilizing single agent or combinations of kinase inhibitors targeting downstream of GNAQ/11. Most notable of these, MEK inhibition with selumetinib showed promising response rates in a phase II clinical trial but missed its clinical endpoint in a phase III trial. Interestingly, there is evidence that UM avoids robust apoptotic cell death in response to kinase inhibitors via autophagic protection. This prevention of robust cell death may translate to poor efficacy in the clinic.

There are no current targeted drug treatments for uveal melanoma and the mutations associated with UM. Accordingly, there is a need for an effective standard therapy or treatment that can improve overall survival in patients having UM.

SUMMARY

In view of evidence that shows uveal melanoma avoids robust apoptotic cell death in response to kinase inhibitors via autophagic protection, direct activation of procaspase-3 in combination with kinase inhibition was investigated for inducing high levels of apoptotic cell death in uveal melanoma. The combination of PAC-1 and certain kinase inhibitors was found to effectively kill melanoma cells with little or no effect on normal (non-cancerous) cells. Accordingly, this disclosure provides a composition comprising:

(a) the compound PAC-1:

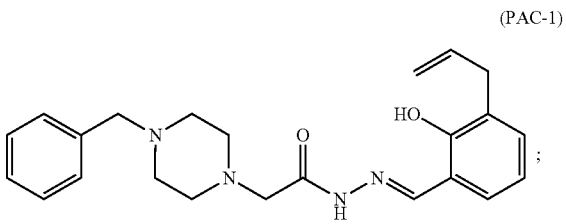 [SMILES: C=CCc1cccc(/C=N/NC(=O)CN2CCN(Cc3ccccc3)CC2)c1O]

(PAC-1)

(b) at least one second active agent, wherein the second active agent is an inhibitor of a tyrosine kinase, an inhibitor of adenosine monophosphate-activated protein kinase (AMPK), or a combination thereof; and (c) optionally a pharmaceutically acceptable diluent, excipient, carrier, or a combination thereof.

In some embodiments, the second active agent is entrectinib, dorsomorphin, or a combination thereof.

This disclosure also provides a method of inhibiting the growth or proliferation of (melanoma) cancer cells comprising contacting the cancer cells with an effective amount of a composition described herein, thereby inhibiting the growth or proliferation of the cancer cells. Additionally, this disclosure provides a method of inducing apoptosis in melanoma cells comprising contacting the cells with an effective amount of a composition described herein, wherein apoptosis is thereby induced in the melanoma cells.

This disclosure also provides a method of treating a cancer, e.g., melanoma, comprising administering to a patient in need thereof, concurrently or sequentially, a therapeutically effective amount of the compound PAC-1 and an effective amount of a second active agent, thereby optionally systemically forming the composition described above, wherein the cancer is thereby treated. In various embodiments, the cancer is uveal melanoma or cutaneous melanoma.

The invention thus provides novel compositions, and compositions for the manufacture of medicaments useful for the treatment of cancer in a mammal, such as an adult human or a non-adult human.

The invention provides for the use of the compositions described herein for use in medical therapy. The medical therapy can be treating cancer, for example, skin cancer (melanoma) or eye cancer (uveal melanoma). The invention also provides for the use of a composition as described herein for the manufacture of a medicament to treat a disease in a mammal, for example, melanoma in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

$$CI = \frac{(D)_1}{(Dx)_1} + \frac{(D)^2}{(Dx)_2}$$

Figure 1:
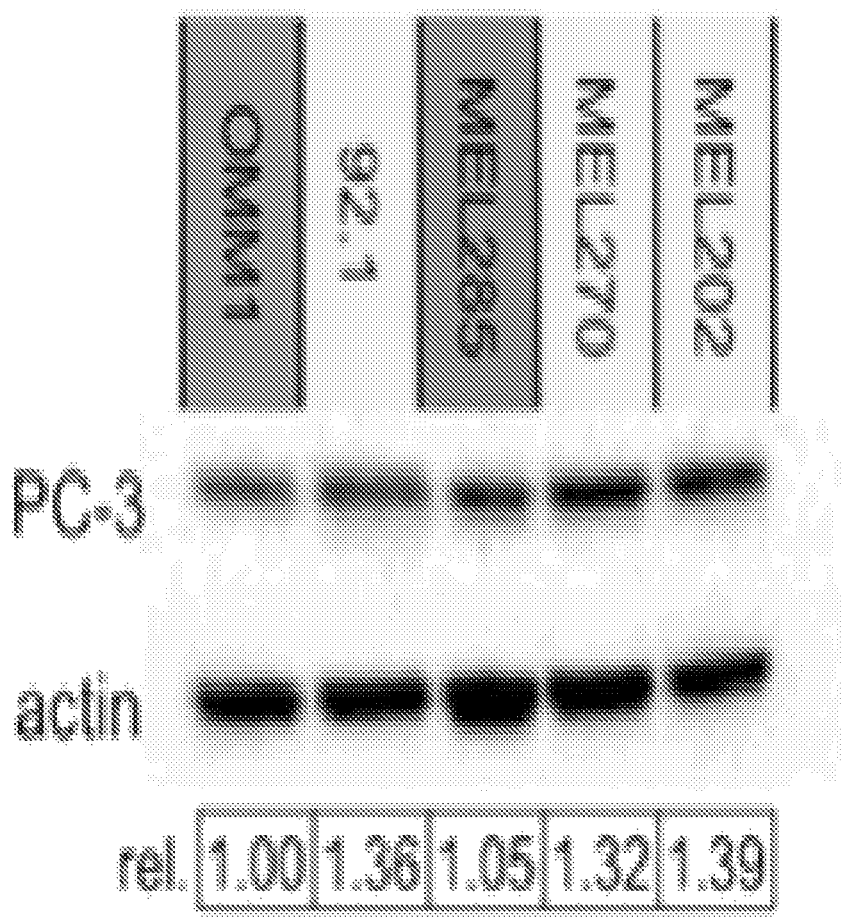
FIG. 1. Relative expression of procaspase-3 (PC-3) across a panel of uveal melanoma cell lines.

where $D_n$=Combination doses of drug n yielding 50% growth inhibition; $Dx_n$=Single doses of drug n yielding 50% growth inhibition.

DETAILED DESCRIPTION

Members of the caspase family of cysteine proteases are key players in both the initiation and execution of apoptosis. Most critical to apoptosis is the proteolytic conversion of procaspase-3 to caspase-3. As both the intrinsic and extrinsic apoptotic pathways converge to activate procaspase-3, and as caspase-3 has over 100 cellular substrates, the activation of procaspase-3 to caspase-3 is a pivotal and committed event in the apoptotic cascade. Procaspase-3 levels are elevated in a variety of tumors including glioblastoma, breast cancer, colon cancer, lung cancer, lymphoma, neuroblastoma, melanoma, and liver cancer. Procaspase-activating compounds 1 (PAC-1) is a small molecule, which enhances procaspase-3 activity in vitro, induces apoptotic death of cancer cells in culture, and has efficacy in multiple mouse xenograft models. There is a strong correlation between cellular procaspase-3 levels and the apoptosis-inducing properties of PAC-1. As described herein, the combination of PAC-1 and certain kinase inhibitors has been found to effectively kill melanoma cells with little or no effect on normal (non-cancerous) cells.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the term "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Uveal Melanoma. The term "uveal melanoma" refers to a cancer (melanoma) of the eye involving parts of the eye collectively referred to as the uvea. Uveal melanoma arises from the uveal tract of the eye, which includes the choroid, ciliary body, and iris. Tumors typically arise from the pigment cells (melanocytes) that reside within the uvea. Uveal melanoma is the most common primary intraocular malignancy in adults. It is biologically different from cutaneous melanoma and accounts for approximately 3% to 5% of all melanoma. There are currently no approved or effective systemic treatment option for individuals with metastatic uveal melanoma. Mutations in GNAQ or GNA11 are found in 80% of uveal melanomas, resulting in constitutive activation of the RAS/RAF/MEK/ERK pathway.

True iris melanomas, originating from within the iris as opposed to originating elsewhere and invading the iris, are distinct in their etiology and prognosis, such that the other tumors are often referred to collectively as posterior uveal melanomas. Iris melanomas share more in common with cutaneous (skin) melanomas in that they frequently harbor BRAF mutations associated with ultraviolet damage.

Cutaneous melanoma is a cancer that starts in the pigment-producing cells of the skin, known as melanocytes. Whereas, non-cutaneous melanomas show up in places not typically thought of as skin as skin, such as eyes, inside of the nose, mucous membranes (e.g., inside the mouth, intestine, vagina, anus, or rectum).

Embodiments of the Invention

This disclosure provides various embodiments of a composition comprising:
(a) the compound PAC-1:

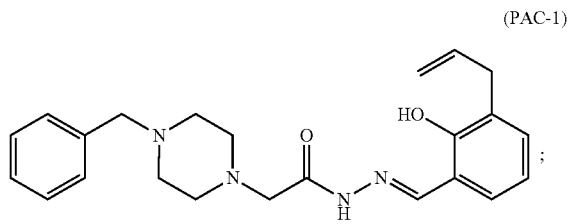 [SMILES: C=CCc1cccc(/C=N/NC(=O)CN2CCN(Cc3ccccc3)CC2)c1O]

(PAC-1)

(b) at least one second active agent, wherein the second active agent is an inhibitor of a tyrosine kinase, an inhibitor of adenosine monophosphate-activated protein kinase (AMPK), or a combination thereof; and
(c) optionally a pharmaceutically acceptable diluent, excipient, carrier, or a combination thereof.

In some embodiments, the second active agent is an inhibitor of a neurotrophic receptor tyrosine kinase (NTRK), C-ros oncogene 1 (ROS1), anaplastic lymphoma kinase (ALK), or a combination thereof. In other embodiments, the second active agent is an inhibitor of tropomyosin receptor kinase A (TrkA), tropomyosin receptor kinase B (TrkB), tropomyosin receptor kinase C (TrkC), or a combination thereof. In further embodiments, the second active agent is an inhibitor of janus kinase 1 (JAK1), janus kinase 2 (JAK2), janus kinase 3 (JAK3), activated CDC42 kinase 1 (ACK1), insulin-like growth factor 1 receptor (IGF1R), focal adhesion kinase (FAK), fms like tyrosine kinase 3 (FLT3), breast tumor kinase (BRK), insulin receptor (IR), aurora-2 kinase (AUR2), RET receptor tyrosine kinase (RET), non-receptor tyrosine-protein kinase 1 (TNK1), or a combination thereof.

In additional embodiments, the second active agent is entrectinib. In yet other embodiments, the second active agent is dorsomorphin. In further embodiments, the second active agent is linsitinib or VS-4718 (PND-1186). In various additional embodiments, the second active agent is R1507, MK0646, OSI-906, BIIB022, figitumumab (CP-751,871), AXL1717, AMG479, alectinib, sunitinib, imatinib, sorafenib, nilotinib, bevacizumab, ipilimumab, cixutumumab, or a combination thereof.

In various embodiments the second active agent is an inhibitor shown for the target in Table A (below):

| Target | Inhibitor | Target | Inhibitor |
|---|---|---|---|
| NTRK | larotrectinib | JAK2 | GW441756 |
| ROS1 | crizotinib | JAK3 | tofacitinib |
| ALK | lorlatinib | ACK1 | ceritinib |
| TrkA | entrectinib | 1GF1R | linsitinib |
| TrkB | GNF5837 | FAK | defactinib |
| TrkC | CH7057288 | FLT3 | midostaurin |
| JAK1 | filgotinib | BRK | tilfrinib |
| IR | tyrphostin | AUR2 | PHA-680632 |
| RET | pralsetinib | TNK1 | lestaurtinib |

In various embodiments, the second active agent can be one or more compounds disclosed in U.S. Pat. No. 8,299,057 which compounds and the formulas describing them are incorporated herein by reference. In various additional embodiments, the second active agent is an inhibitor of IGF1R wherein the IGF1R inhibitor is AG538, AG1024, NVP-AEW541, or figitumumab. In various other embodiments, the second active agent is an inhibitor of FAK (or protein tyrosine kinase 2 (PTK2)) wherein the FAK inhibitor is PF-573,228, PF-562,271, NVP-226, Y15, defactinib, or VS-6063. In various embodiments, the second active agent is one that can be administered in an amount that is synergistic with PAC-1 for the treatment of uveal melanoma or cutaneous melanoma.

In various embodiments, PAC-1 and/or the second active agent are administered orally, intravenously, subcutaneously, by inhalation, intramuscularly, intravitreally, or any route known to one of skill in the art.

In various other embodiments of the composition disclosed above, the concentration of the second active agent is about 1 nM to about 100 μM. In additional embodiments, the concentration of the second active agent is about 1 nanomolar to about 10,000 nanomolar. In yet other embodiments, the concentration of PAC-1 is about 0.1 µM to about 50 µM. In further embodiments, the concentration of PAC-1 is about 1 µM to about 15 JIM. In yet some other embodiments, the concentration of PAC-1 is about 1 µM to about 5 µM.

In various additional embodiments, the systemic concentration of PAC-1 and the second active agent (SAA) are shown Table B* (below):

|  | SAA (µM) | | | | | | | | |
| --- | --- | --- | --- | --- | --- | --- | --- | --- | --- |
|  | (1) | (2) | (3) | (4) | (5) | (6) | (7) | (8) | (9) |
| PAC-1 (µM) | 0.1-1 | 1-2 | 2-5 | 5-10 | 10-15 | 15-20 | 20-30 | 30-40 | 40-50 |
| (A) 0.1-1 | A1 | A2 | A3 | A4 | A5 | A6 | A7 | A8 | A9 |
| (B) 1-2 | B1 | B2 | B3 | B4 | B5 | B6 | B7 | B8 | B9 |
| (C) 2-5 | C1 | C2 | C3 | C4 | C5 | C6 | C7 | C8 | C9 |
| (D) 5-10 | D1 | D2 | D3 | D4 | D5 | D6 | D7 | D8 | D9 |
| (E) 10-15 | E1 | E2 | E3 | E4 | E5 | E6 | E7 | E8 | E9 |
| (F) 15-20 | F1 | F2 | F3 | F4 | F5 | F6 | F7 | F8 | F9 |
| (G) 20-30 | G1 | G2 | G3 | G4 | G5 | G6 | G7 | G8 | G9 |
| (H) 30-40 | H1 | H2 | H3 | H4 | H5 | H6 | H7 | H8 | H9 |
| (I) 40-50 | I1 | I2 | I3 | I4 | I5 | I6 | I7 | I8 | I9 |

* Units of the recited concentrations (A)-(I) and (1)-(9) are micromolar (µM). PAC-1 concentration ranges are read down the column. SAA concentration ranges are read across the row. Embodiments are designated as a letter and a number. For example, embodiment D2 indicates a PAC-1 concentration of about 5 to about 10 micromolar and a SAA concentration of about 1 to about 2 micromolar.

This disclosure additionally provides a composition described above wherein a) the carrier comprises water, a buffer, a sugar, a cellulose, a cyclodextrin, dimethyl sulfoxide, polyethylene glycol, tocopherol, a liposome, a micelle, or a combination thereof, and/or b) the excipient comprises, a binder, a lubricant, a sorbent, a vehicle, a disintegrant, a preservative, or a combination thereof.

This disclosure provides a method of inhibiting the growth or proliferation of (melanoma) cancer cells comprising contacting cancer cells with an effective amount of the composition described herein, thereby inhibiting the growth or proliferation of the cancer cells. Furthermore, this disclosure provides a method of inducing apoptosis in a (melanoma) cancer cell comprising contacting the cancer cell with an effective amount of the composition disclosed herein, wherein apoptosis is thereby induced in the cancer cell.

Additionally, this disclosure also provides a method of treating a cancer (melanoma) comprising administering to a patient in need thereof, concurrently or sequentially, a therapeutically effective amount of the compound PAC-1 and an effective amount of a second active agent, to optionally systemically form a composition described herein, wherein the cancer is thereby treated. In various embodiments, PAC-1 is synergistic with the second active agent wherein the second active agent is entrectinib, dorsomorphin, or a compound from Table A, wherein the concentrations of the agents can be those recited in Table B.

In various embodiments of the disclosure, the cancer is uveal melanoma or cutaneous melanoma. In other embodiments, the uveal melanoma is a GNAQ mutant, GNA11 mutant, GNAQ wild type, or GNA11 wild type, uveal melanoma. In additional embodiments, a resistance to treatment of the cancer in the patient in need thereof is reduced, delayed, or eliminated. In yet other embodiments, a metastasis of the cancer in the patient in need thereof is reduced, delayed, or eliminated. The reduced, delayed or eliminated metastasis of the cancer can be determined by procedures known to ordinary persons skilled in the art.

This disclosure also provides a method wherein PAC-1 synergizes with the second active agent in vivo, wherein:
a) the concentration of PAC-1 is about 0.1 µM to about 50 µM, and the concentration of the second active agent is about 1 nM to about 100 µM;
b) the concentration of PAC-1 is about 1 µM to about 15 µM, and the concentration of the second active agent is about 1 nM to about 10,000 nM; or
c) the concentration of PAC-1 is about 1 µM to about 5 µM, and the concentration of the second active agent is about 1 nM to about 1000 nM.

In other embodiments of the disclosure herein, the concentration of PAC-1 is about 0.5 µM, about 1.5 µM, about 2 µM, about 2.5 µM, about 3 µM, about 3.5 µM, about 4 µM, about 4.5 µM, about 5 µM, about 6 µM, about 7 µM, about 8 µM, about 9 µM, or about 10 µM.

In some embodiments, the compound PAC-1 and the second active agent are concurrently administered to the cancer patient. In other embodiments, PAC-1 and the second active agent are sequentially administered to the cancer patient. In one embodiment, PAC-1 is administered to the cancer patient before the second active agent. In another embodiment, PAC-1 is administered to the cancer patient after the second active agent. In certain embodiments, the second active agent is entrectinib, dorsomorphin, linsitinib, VS-4718, or a combination thereof.

This disclosure further provides a use of a composition, or a combination of compositions, disclosed herein to prepare a medicament for the treatment of melanoma. The compositions can be a composition comprising PAC-1, a composition comprising a second active agent, such as entrectinib, or a combination thereof, or a composition comprising PAC-1 and a second active agent.

In various embodiments, the melanoma is uveal melanoma or cutaneous melanoma. In various additional embodiments, the uveal melanoma has the GNAQ mutation or GNA11 mutation, or is the GNAQ wild type or GNA11 wild type.

In various embodiments, the dose, e.g., daily dose, of PAC-1 and the second active agent (SAA) are shown Table C* (below):

|  | SAA (mg) | | | | | | | | |
| --- | --- | --- | --- | --- | --- | --- | --- | --- | --- |
|  | (1) | (2) | (3) | (4) | (5) | (6) | (7) | (8) | (9) |
| PAC-1 (mg) | 1-25 | 25-50 | 50-100 | 100-200 | 200-300 | 300-400 | 400-500 | 500-650 | 650-850 |
| (A) 1-25 | A1 | A2 | A3 | A4 | A5 | A6 | A7 | A8 | A9 |
| (B) 25-50 | B1 | B2 | B3 | B4 | B5 | B6 | B7 | B8 | B9 |
| (C) 50-100 | C1 | C2 | C3 | C4 | C5 | C6 | C7 | C8 | C9 |
| (D) 100-200 | D1 | D2 | D3 | D4 | D5 | D6 | D7 | D8 | D9 |
| (E) 200-300 | E1 | E2 | E3 | E4 | E5 | E6 | E7 | E8 | E9 |
| (F) 300-400 | F1 | F2 | F3 | F4 | F5 | F6 | F7 | F8 | F9 |

-continued

| | SAA (mg) | | | | | | | | |
|---|---|---|---|---|---|---|---|---|---|
| PAC-1 (mg) | (1) 1-25 | (2) 25-50 | (3) 50-100 | (4) 100-200 | (5) 200-300 | (6) 300-400 | (7) 400-500 | (8) 500-650 | (9) 650-850 |
| (G) 400-500 | G1 | G2 | G3 | G4 | G5 | G6 | G7 | G8 | G9 |
| (H) 500-650 | H1 | H2 | H3 | H4 | H5 | H6 | H7 | H8 | H9 |
| (I) 650-850 | I1 | I2 | I3 | I4 | I5 | I6 | I7 | I8 | I9 |

* Dosage units of the recited concentrations (A)-(I) and (1)-(9) are milligrams (mg). PAC-1 dose ranges are read down the column. SAA dose ranges are read across the row. Embodiments are designated as a letter and a number. For example, embodiment D2 indicates a PAC-1 dose of about 200 to about 300 milligrams and a SAA dose of about 50 to about 100 milligrams.

As would be recognized by one of skill in the art, recitation of a specific concentration or concentration range herein can be exchanged with a suitable dosage amount or dosage range, for example, a range or endpoint of a range recited in Table C above, or as discussed below. In various embodiments, the amounts of PAC-1 and the second active agent administered are amounts that are synergistic for the treatment of uveal melanoma or cutaneous melanoma.

In other embodiments the total dose of PAC-1 is about 75 mg, about 150 mg, about 250 mg, about 375 mg, about 450 mg, about 625 mg, about 750 mg, or about 825 mg, wherein the total dose is administered once a day, twice a day, or three times a day.

This disclosure provides various embodiments of a combination of a second active agent (SAA) and a compound PAC-1 for use in a method of treating a cancer (e.g., melanoma) in a patient in need thereof, the use comprising administering to a patient, concurrently or sequentially, a therapeutically effective amount of the SAA and an effective amount of the compound PAC-1, wherein the cancer is thereby treated. Another embodiment provides a composition of PAC-1 and a composition of entrectinib for use in a method of treating uveal melanoma or cutaneous melanoma in a patient in need thereof, the use comprising administering to a patient, concurrently or sequentially, a therapeutically effective amount of the composition of PAC-1 and a therapeutically effective amount of the composition of entrectinib, wherein the uveal melanoma or cutaneous melanoma is thereby treated. The therapeutically effective amounts can be amounts that are synergistic when administered for the treatment of uveal melanoma or cutaneous melanoma.

Other embodiments provide a combination of the SAA and the compound PAC-1 for the said use, wherein the SAA and the compound PAC-1 are administered concurrently. Other embodiments provide a combination of the SAA and the compound PAC-1 for said use, wherein the SAA and the compound PAC-1 are administered sequentially. Other embodiments provide a combination of the SAA and the compound PAC-1 for said use, wherein the SAA is administered before the compound PAC-1. Other embodiments provide a combination of the SAA and the compound PAC-1 for said use, wherein the SAA is administered after the compound PAC-1.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

Procaspase-3 Activation Strategy in UM Cell Lines.

Procaspase-3 activating compound, PAC-1, has been shown to be a potent activator of procaspase-3 to active caspase-3, inducing apoptosis. UM cell lines express procaspase-3 (FIG. 1), and PAC-1 has activity as a single agent in a panel of UM cell lines (Table D).

TABLE D $IC_{50}$ values of PAC-1 in a panel of uveal melanoma cell lines following 72-hour incubation. Values shown are an average of three independent experiments and error is reported as s.e.m.

| | Mutation | Cell Line | $IC_{50}$ (µM) |
|---|---|---|---|
| GNAQ Mutant | Q209L | 92.1 | 3.6 ± 0.7 |
| | Q209L, R210K | MEL202 | 10.3 ± 0.2 |
| | Q209P | MEL270 | 9.8 ± 0.6 |
| | Q209P | OMM2.5 | 9.5 ± 0.5 |
| GNA11 Mutant | Q209L | OMM1 | 4.0 ± 0.8 |
| GNAQ/11 WT | WT | MEL285 | 7.4 ± 2.6 |
| | WT | MEL290 | 11.7 ± 1.2 |

Current Treatment of Uveal Melanoma.

There are more than 40 clinical trials reported in uveal melanoma with average response rate of 4%. Current standard of care is dacarbazine. In a recent randomized clinical SUMMIT trial of selumetinib in combination with dacarbazine in patients with metastatic uveal melanoma the objective response rate was 3%, progression free survival of 2.8 months in selumetinib plus dacarbazine treatment group. Three- and 6-month PFS rates were 38% and 10%, respectively. Overall survival was only 10 months.

Entrectinib.

Entrectinib is a potent tyrosine kinase inhibitor that targets oncogenic rearrangements in NTRK, ROS1, and ALK. Two phase I trials demonstrated activity in tyrosine kinase inhibitor-naïve patients along with substantial intracranial activity. In ROS1-rearranged lung cancers, entrectinib resulted in durable disease control and prolonged progression-free survival. The drug was well tolerated and has a safety profile that includes adverse events mediated by on-target tropomyosin-related kinase A/B/C inhibition. The most common treatment-related adverse events of any grade were fatigue/asthenia (46%, n=55/119), dysgeusia (42%, n=50/119), paresthesias, (29%, n=34/119), nausea (28%, n=33/119), and myalgias (23%, n=27/119).

Combining PAC-1 and Therapeutically Relevant Inhibitors.

PAC-1 has been shown to synergize with a variety of clinically relevant agents, including kinase inhibitors (*Mol. Cancer Ther.* 2016, 15, 1859; *Cell Chem. Biol.* 2018, 25, 996). This synergy was leveraged by screening PAC-1 in combination with a variety of clinically relevant kinase inhibitors. The results of this biased screen are presented in FIG. 2.

Figure 2:
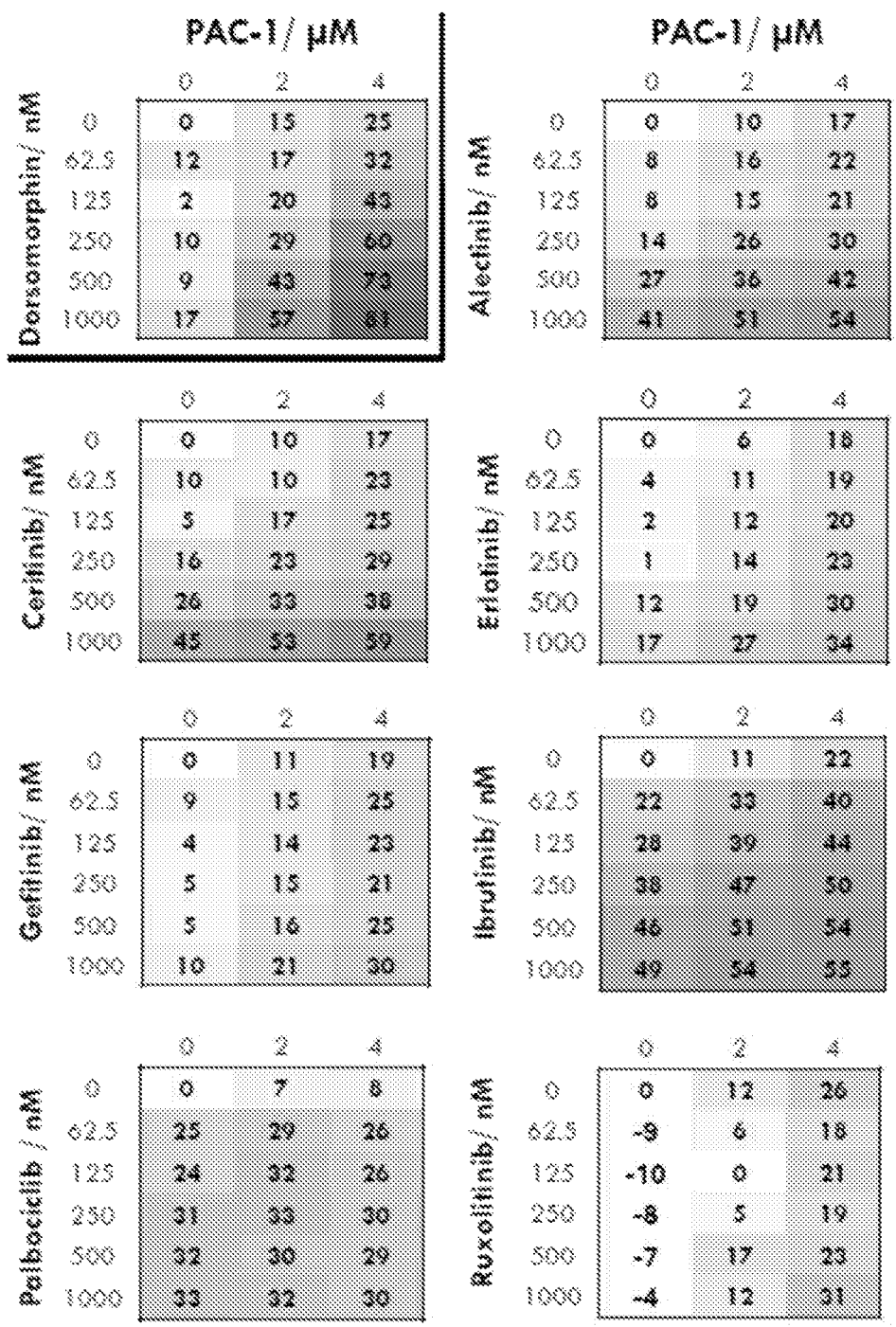
FIG. 2. Percent cell death observed when the UM cell line MEL270 was treated with the combination of PAC-1 and small molecule inhibitors, 72-hour incubation. MEL270 is a GNAQ mutant cell line. The data from the PAC-1+entrectinib combination is shown in the box. Data shown is the average of two independent experiments.
Figure 2:
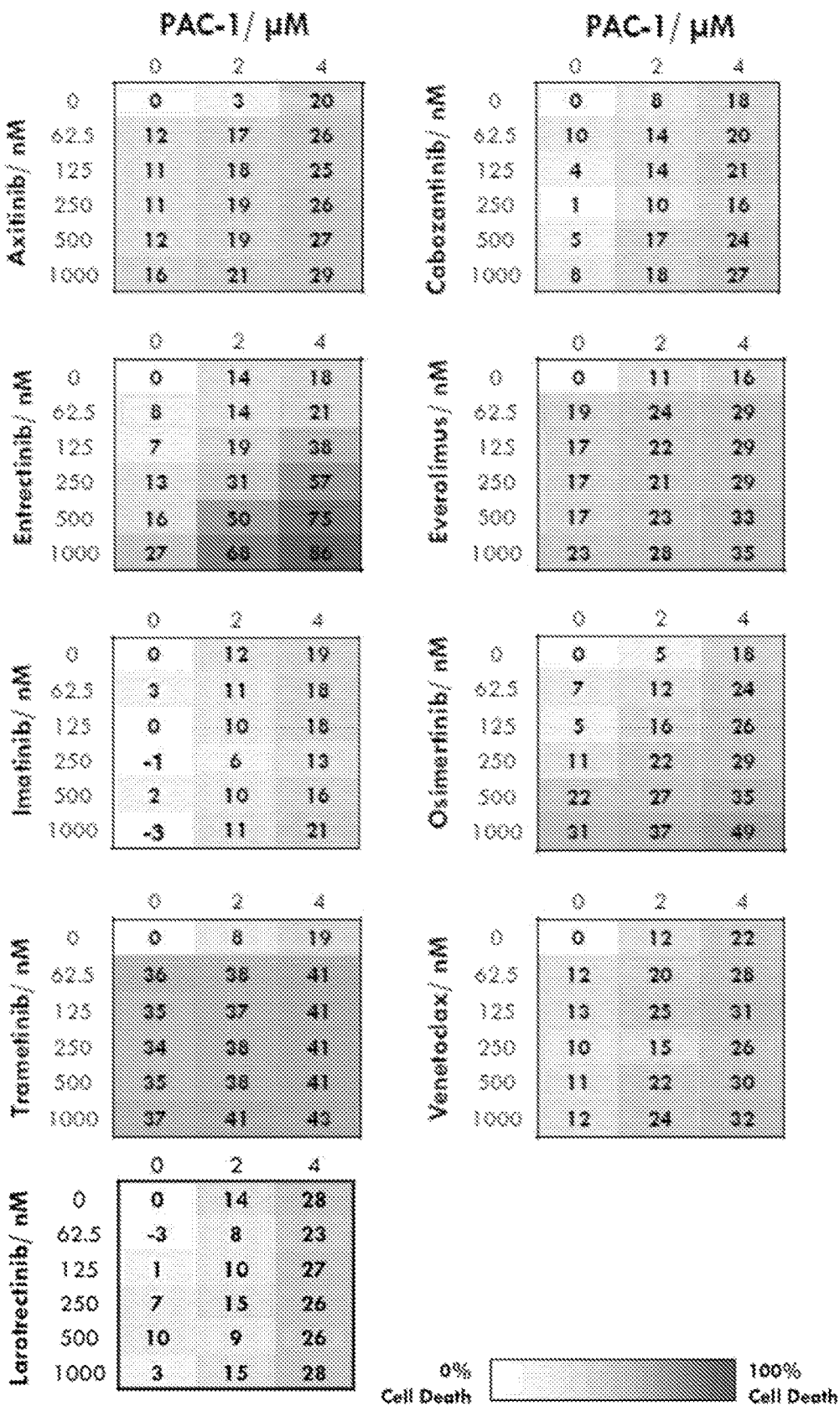
Figure 3:
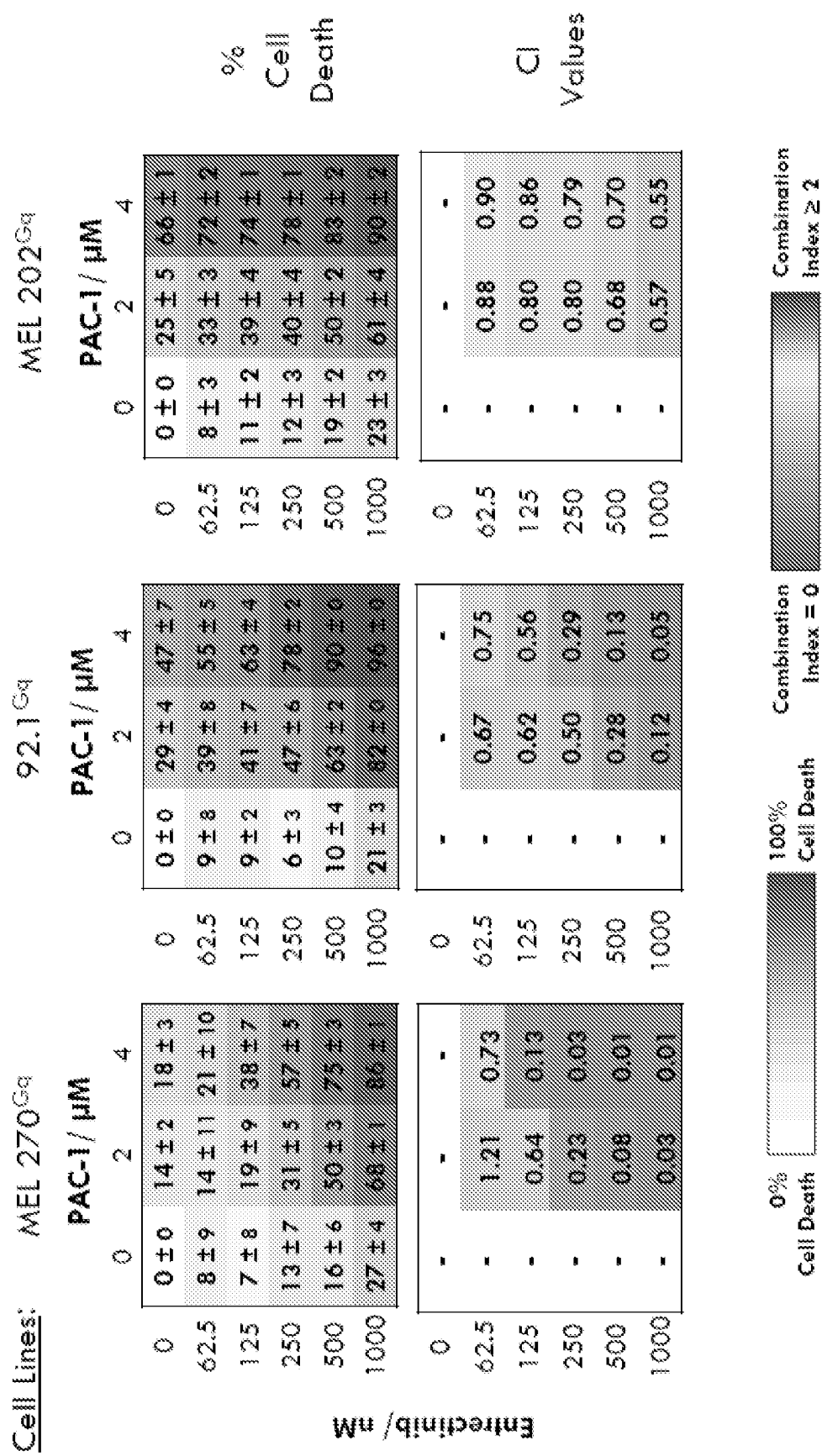
FIG. 3. PAC-1 in combination with entrectinib shows synergy across a panel of UM cell lines. Cell death and corresponding CI values were calculated after 72-hour incubation. Cell lines are denoted by their driver mutation. CI values<1 are synergistic, with the lower values representing higher level of synergy. CI values=1 indicate an additive effect. CI values>1 designate an antagonist effect between the two agents. Data shown is the average of at least three independent experiments except for the H460KRAS cell lines; error is expressed as s.e.m.; 4,000 cells/well, Alamar Blue Fluorescence; Dead Control: Raptinal.
Figure 3:
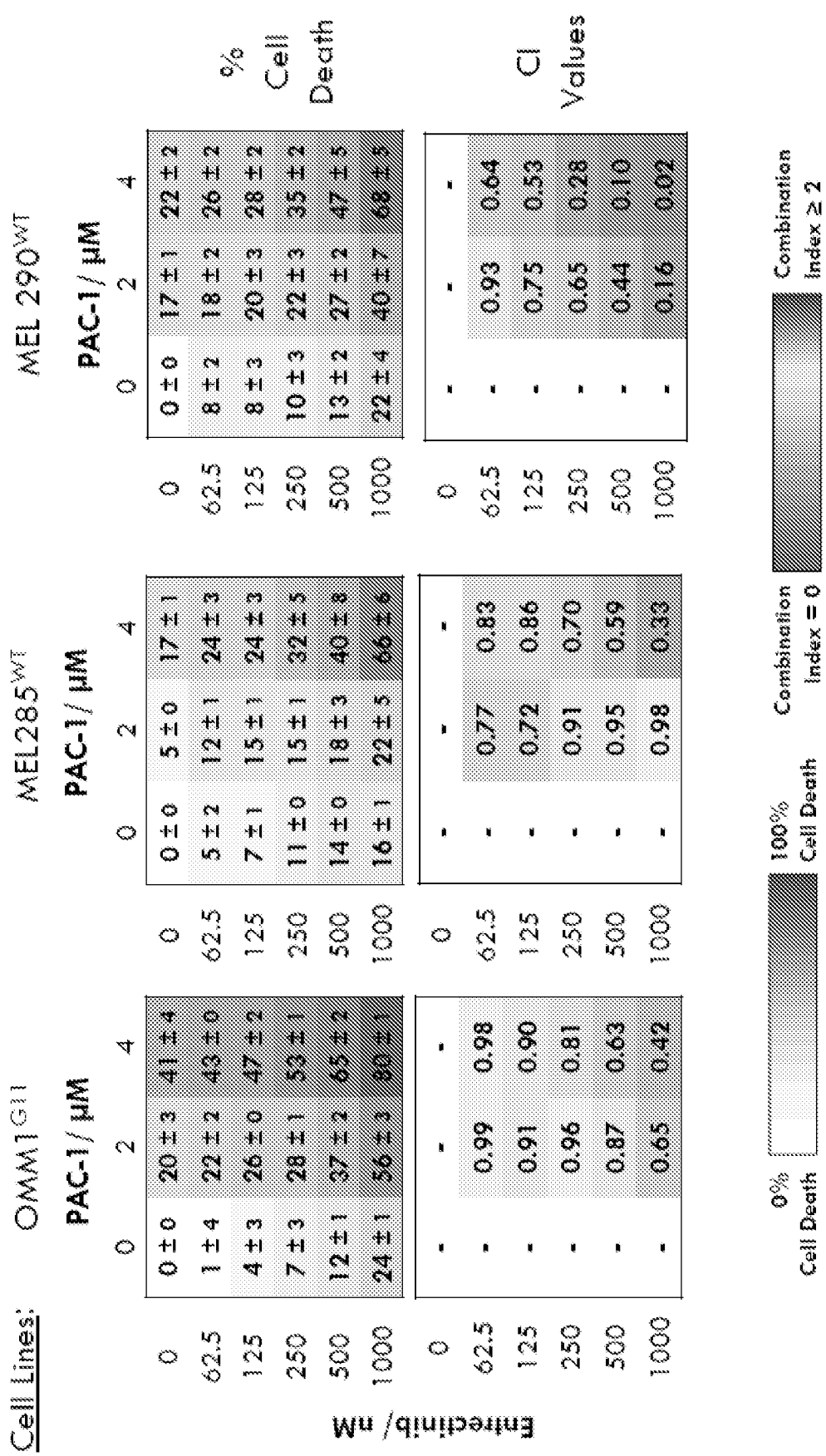
Figure 3:
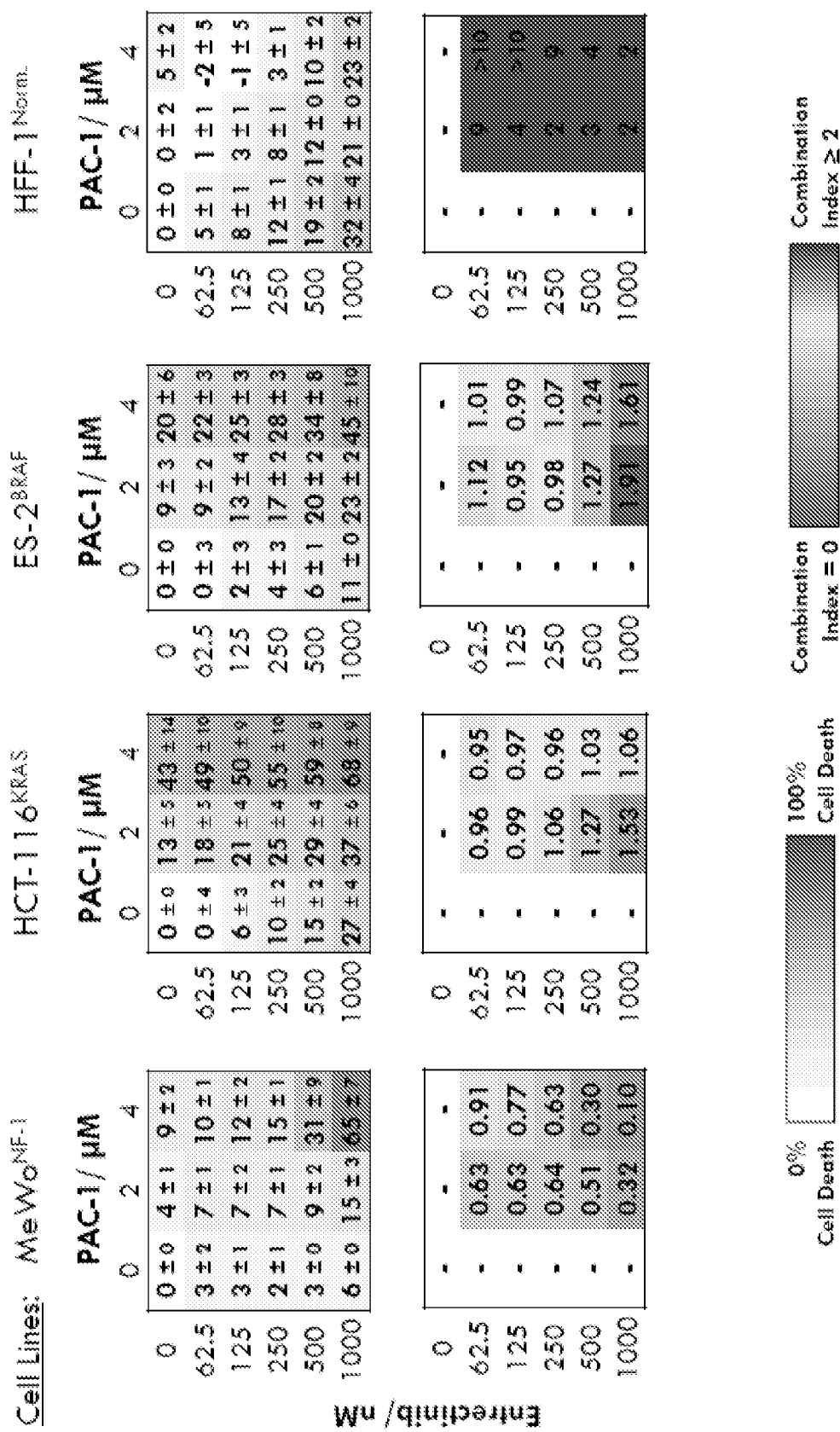
Figure 3:
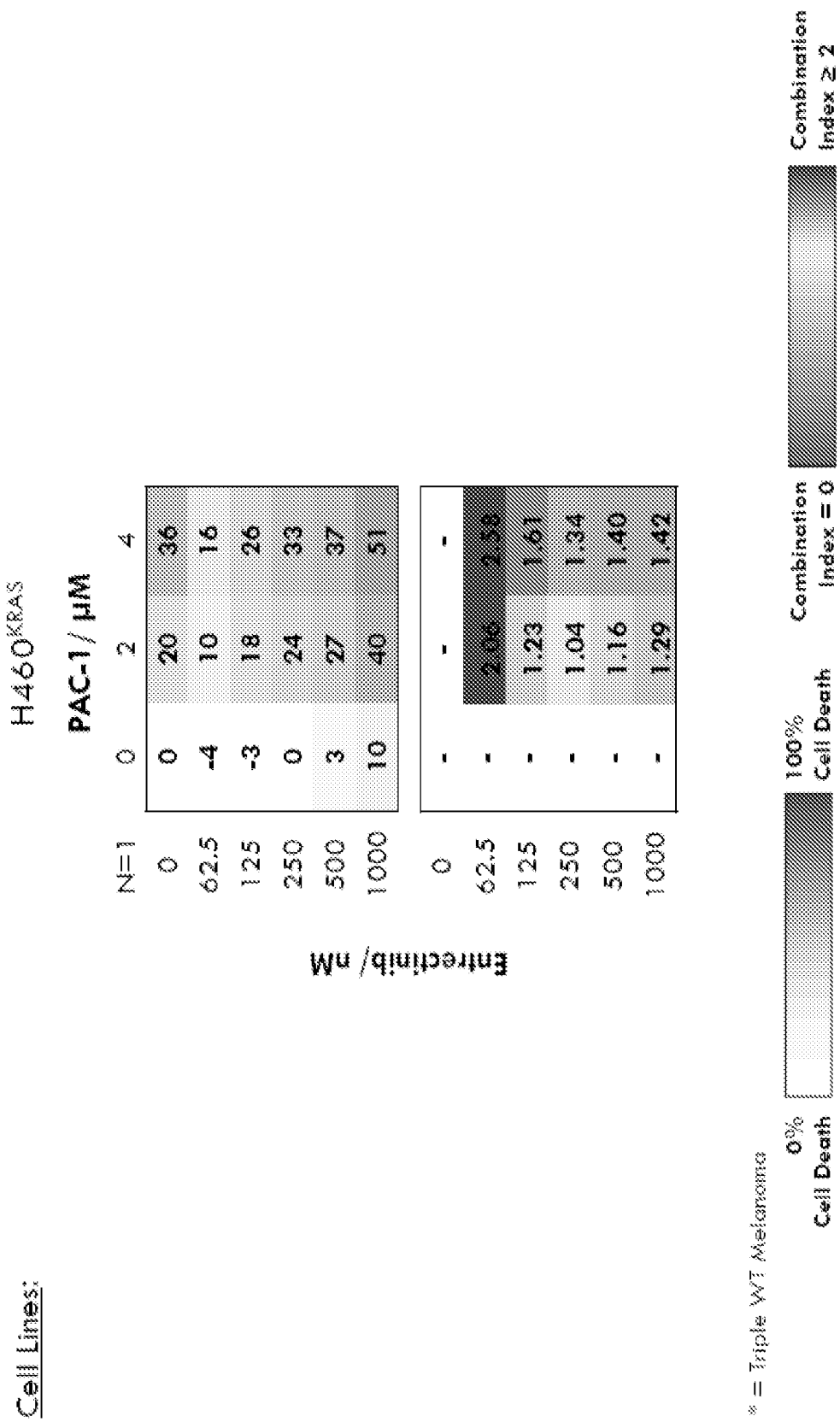

The combination of PAC-1 and entrectinib clearly stands out from this screen; for example, concentrations of PAC-1 and entrectinib that give ~16% death each as a single agent induce 75% death in combination (FIG. 2). Entrectinib is a pan-TRK fusion, ALK fusion, and ROS1 fusion kinase inhibitor. These three types of fusion proteins are key driver alterations in multiple cancer types. Interestingly, these fusions, their parental kinases, and/or off-target kinases are not reported as major oncogenic drivers in UM and may point to an unexplored therapeutic avenue in UM. To explore this combination further, the observed synergy was quantified across a panel of UM cell lines (FIG. 3).

Figure 4:
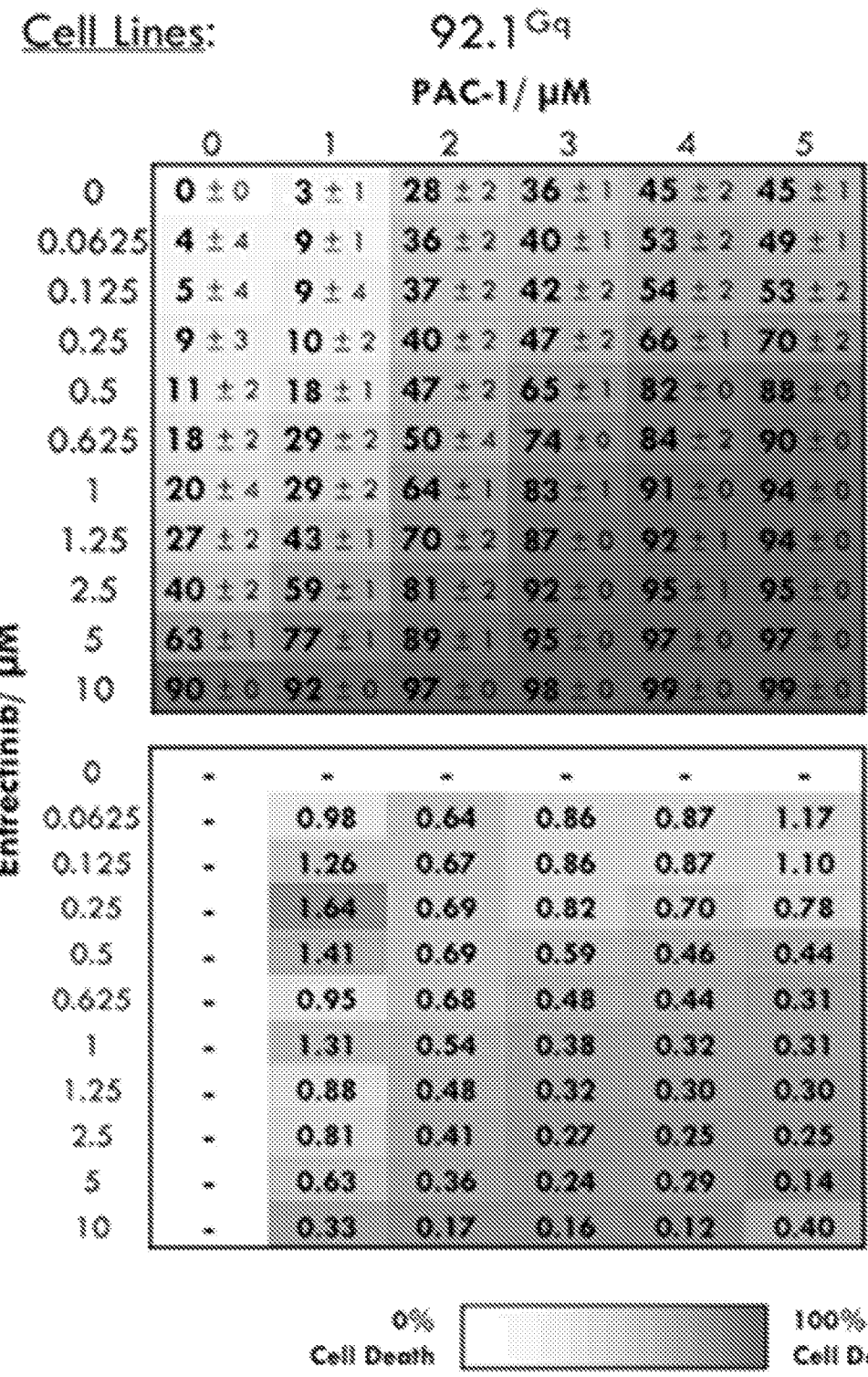
FIG. 4. PAC-1+entrectinib shows broad synergy across a wide concentration range. Data shown is the average of at least three independent replicates and error is represented by s.e.m.
Figure 4:

Interestingly, the greatest responses (as measured by cell death and CI value) were observed in GNAQ/11 cell lines. While cell death was lower in GNAQ/11 WT cells (MEL285 & MEL290), CI values were below one, implying a synergistic effect in these cell lines. This effect seen in mutant GNAQ UM cell lines was consistent across a broad range of PAC-1 and entrectinib concentrations (FIG. 4).

Figure 5:
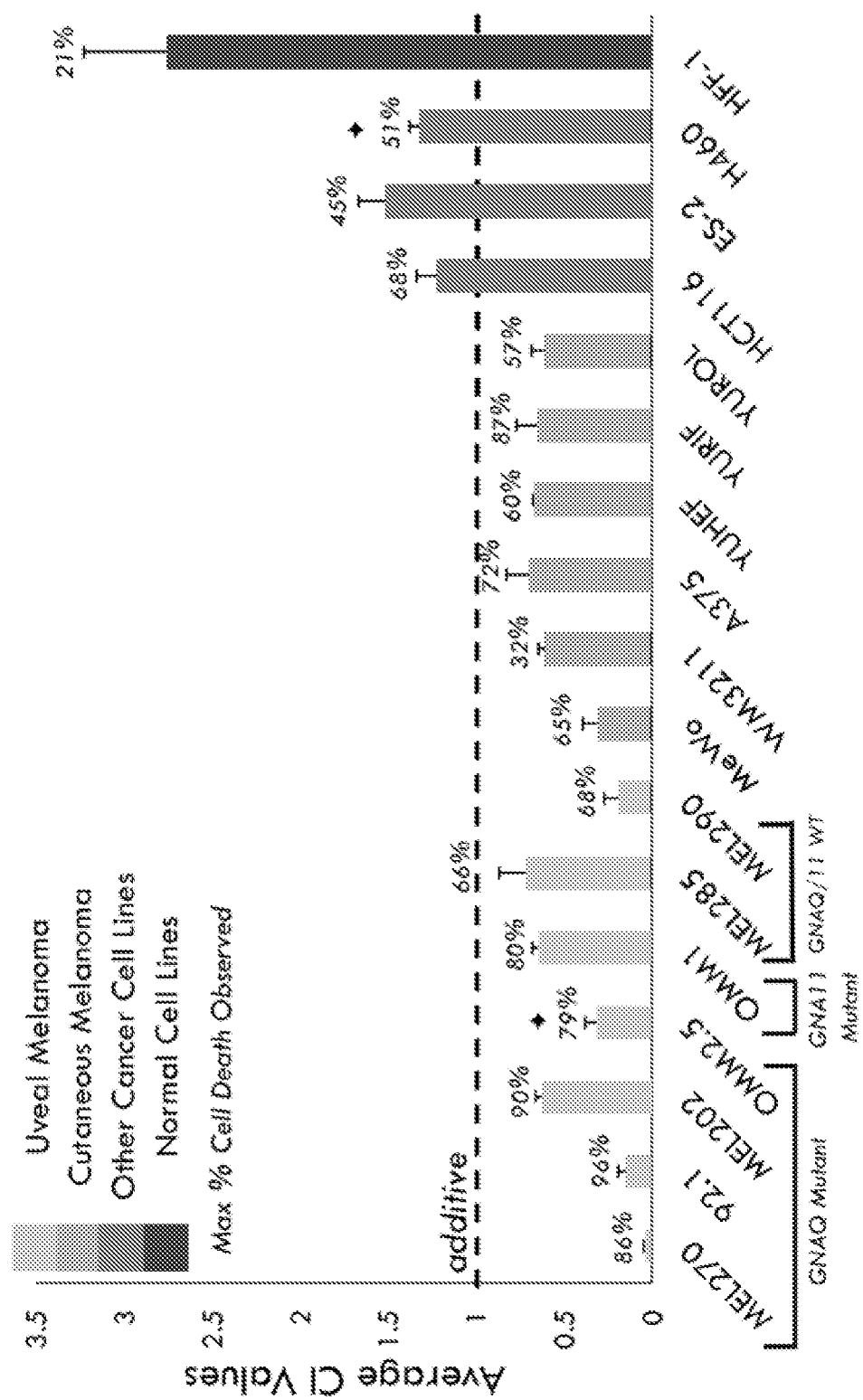
FIG. 5. PAC-1+entrectinib has significant activity toward UM cell lines. Average CI was calculated by averaging the cell death observed at 2 µM PAC-1+0.5 µM entrectinib, 2 µM PAC-1+1 µM entrectinib, 4 µM PAC-1+0.5 µM entrectinib, and 4 µM PAC-1+1 µM entrectinib. Values shown are the average of at least two independent experiments and error is s.e.m. of the average, unless otherwise denoted. ◆=represents N=1 result.
Figure 6:
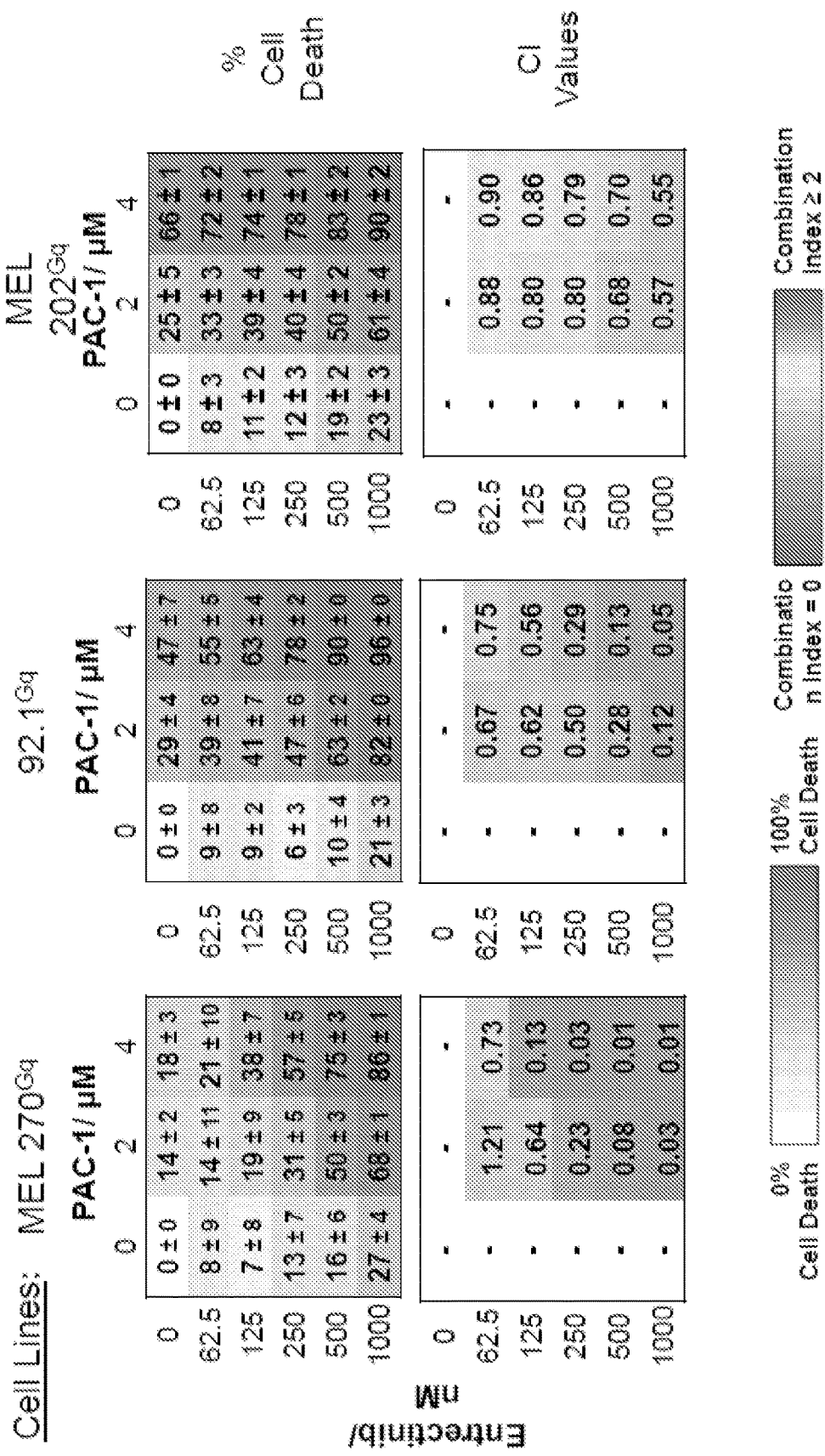
FIG. 6. Data shown is the average of at least three independent experiments; error is expressed as s.e.m.; 4,000 cells/well, 72-hour incubation, Alamar Blue Fluorescence; Dead Control: Raptinal. (A) PAC-1 and entrectinib synergize in $UM^{Gq}$. (B) PAC-1 and entrectinib synergize in $UM^{G11/WT}$. (C) Interpretation of Combination Index (CI)
Figure 6:
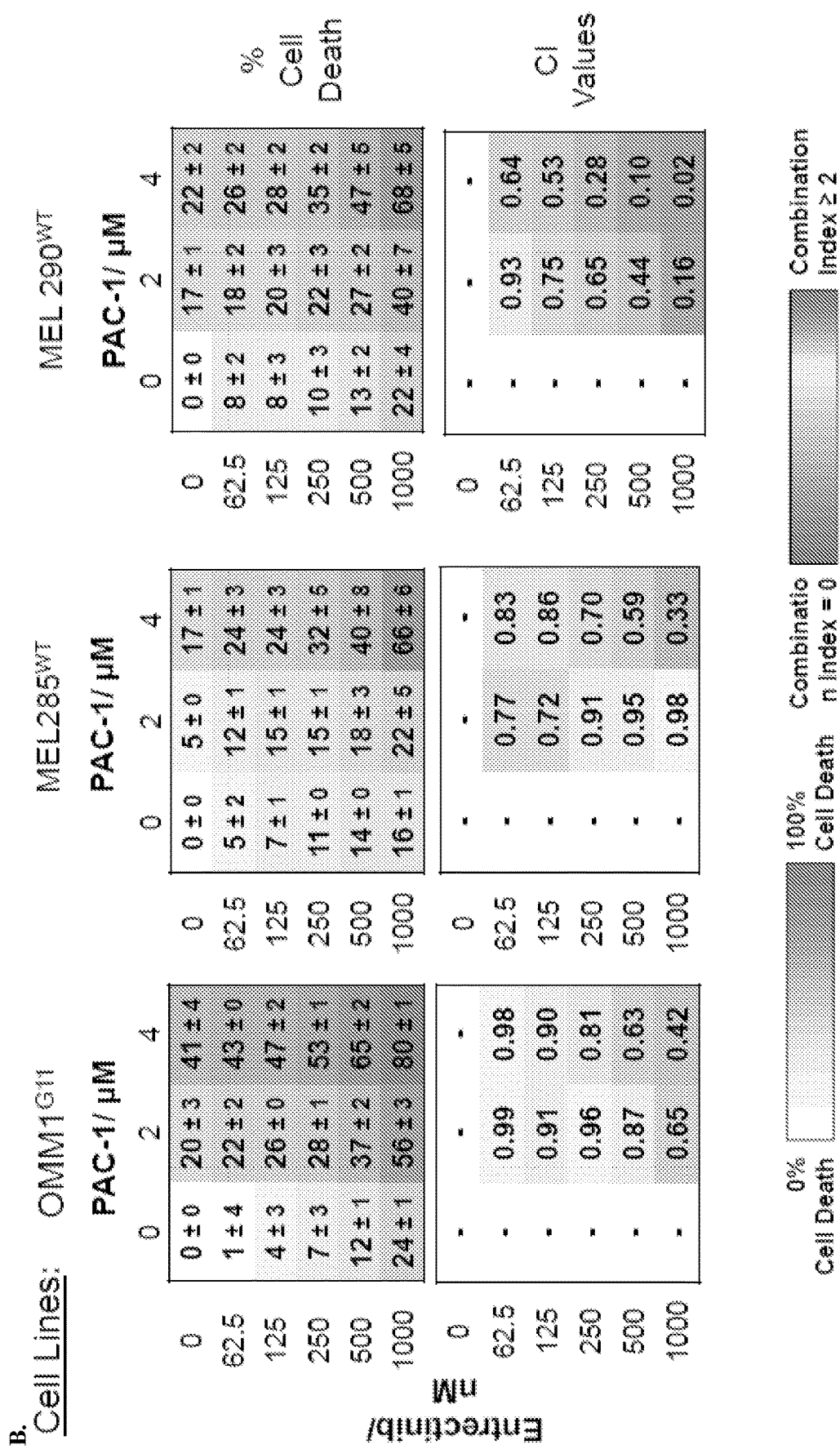

Because the target of entrectinib in UM cells has not been elucidated, determining if this combination would be synergistic was sought across a panel of cancer cell lines (FIG. 5). The combination of PAC-1 and entrectinib appears to be most effective and synergistic in UM GNAQ/11 mutant cell lines. The average CI value in other melanoma cell lines is also below one, indicating a synergistic combination, while the other cancer cell lines evaluated do not show synergy (FIG. 5). Importantly, this combination did not lead to significant cell death and was not synergistic in HFF-1, a non-cancerous, normal cell line.

The results described herein present a novel strategy for treatment of uveal melanoma. PAC-1 and entrectinib in combination has proven to be an exciting prospect for clinical therapy for uveal and cutaneous melanoma. Entrectinib completed two Phase I clinical trials with promising activity and limited toxicity in patients, and PAC-1 is currently undergoing a Phase I clinical trial in humans. Therefore, the combination therapy of entrectinib plus PAC-1 is expected to provide an effective clinical treatment for uveal melanoma and closely related cancers.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds and compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds and compositions described herein can be effective as anti-cancer agents and have higher efficacy and/or reduced toxicity as compared to, for example, entrectinib, when used alone to treat a cancer at standard single-drug effective doses.

The invention provides therapeutic methods of treating cancer in a mammal (or vertebrates), which, for example, involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, (uveal) melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Clinical Studies

PAC-1 has been dosed in 34 human patients through 7 dose levels of PAC-1 (range: 75-750 mg). Two patients progressed during the first cycle of PAC-1 therapy. Thirty-two patients received PAC-1 for at least 2 dosing cycles (a cycle is 21 days of daily dosing followed by 7 days of no drug). As a result of stable disease responses, six patients received PAC-1 for 4 cycles, three patients received PAC-1 for 6 cycles and two patients received PAC-1 for 10 cycles. No serious adverse events (SAEs) associated with PAC-1 administration have been observed. Further, after careful review of all neurological and neurocognitive assessments and data collected through dose level 7 (750 mg) there were no conclusive signs of neurotoxicity associated with PAC-1 dosing. Nevertheless, the brain tissue changes observed in both GLP dog PK/preclinical PAC-1 toxicity studies highlights the need for continued neurologic and neurocognitive testing and observational diligence in detecting any possible neurological changes associated with PAC-1 exposure.

Preclinical Data on Entrectinib and PAC-1 Activity in Uveal Melanoma

An in vitro study of PAC-1 and entrectinib combination was performed in seven uveal melanoma cell lines (GNAQ mutant; MEL270, 92.1, MEL202, OMM2.5, GNA11 mutant: OMM1, and GNAQ and GNA11 wild type: MEL285, and MEL290). In all seven cell lines a synergistic killing effect of PAC-1 and entrectinib was observed. It is believed that entrectinib synergizes with PAC-1 in human patient with metastatic melanoma and produces superior prolongation of progression free survival.

Objective(s) and Endpoint(s)

Measurement of progression-free survival (PFS) rate, using RECIST v1.1, in subjects with metastatic uveal melanoma treated with entrectinib and PAC-1 is ongoing (Table 1). The safety of entrectinib and PAC-1 combination is being evaluated, assessed by the incidence and severity of drug-related adverse events (AE), in subjects with metastatic uveal melanoma. The objective response rate [complete response (CR)+partial response (PR)], using RECIST v.1.1 and imaging, in subjects with metastatic uveal melanoma treated with entrectinib and PAC-1 is being determined. Duration of response, using RECIST v1.1, in subjects with metastatic uveal melanoma is being determined. Overall survival (OS) rate in subjects with metastatic uveal melanoma treated with entrectinib and PAC-1 is being measured. Procaspase 3 expression in uveal melanoma tissue, and a correlation between DNAQ and DNA11 mutation and presence of procaspase 3 expression are being determined.

TABLE 1

Study Treatment. Dosage levels of either active can be varied from 40 mg to 750 mg.

| Entrectinib (mg) daily orally | PAC-1 (mg) daily orally |
|---|---|
| 40 or 400 | 500 |

| Dose Level | PAC-1 Dose (mg, orally) | Entrectinib (mg, orally) | Number of Patients* |
|---|---|---|---|
| 1 | 500 daily | 400 daily | 3-6 |
| 2 | 500 daily | 600 daily | 3-6 |
| 3 | 625 daily | 600 daily | 3-6 |

Example 2. Pharmaceutical Dosage Forms

The following formulations illustrate representative pharmaceutical dosage forms that may be used for the therapeutic administration of a compound described herein or a compound of a formula described herein, each optionally in the form of pharmaceutically acceptable salt or solvate, and each optionally in combination with one or more of a pharmaceutically acceptable diluent, excipient, or carrier; hereinafter referred to as 'Composition X'. Composition X can include a single agent (e.g., PAC-1 or entrectinib) or Composition X can include the combination of two or more active agents (e.g., PAC-1 and entrectinib). Dosage amounts below are representative only. The amount of active agent and other components in each formulation can be adjusted (e.g., substantially proportionally) for larger or smaller dosage units, or the amount of active agent in each formulation can be adjusted higher or lower for larger or smaller dosage units while maintaining the relative proportions of the other components at the recited levels.

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
| --- | --- |
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
| --- | --- |
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
| --- | --- |
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
| --- | --- |
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
| --- | --- |
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
| --- | --- |
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
| --- | --- |
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
| --- | --- |
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising:
(a) the compound PAC-1:

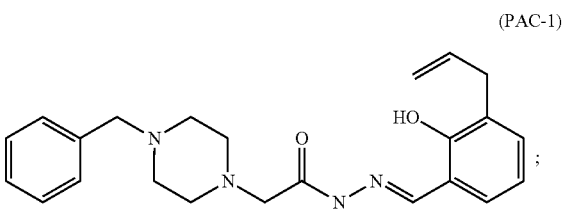

(PAC-1)

(b) at least one second active agent, wherein the second active agent is an inhibitor of C-ros oncogene 1 (ROS1), anaplastic lymphoma kinase (ALK), tropomyosin receptor kinase A (TrkA), tropomyosin receptor kinase B (TrkB), tropomyosin receptor kinase C (TrkC), or a combination thereof; and (c) optionally a pharmaceutically acceptable diluent, excipient, carrier, or a combination thereof.

2. The composition of claim 1 wherein the second active agent is an inhibitor of C-ros oncogene 1 (ROS1), anaplastic lymphoma kinase (ALK), tropomyosin receptor kinase A (TrkA), tropomyosin receptor kinase B (TrkB), and tropomyosin receptor kinase C (TrkC).

3. The composition of claim 1 wherein the second active agent is entrectinib.

4. The composition of claim 1 wherein the concentration of the second active agent is about 62.5 nM to about 10 µM.

5. The composition of claim 1 wherein the concentration of the second active agent is about 1 nM to about 1 µM.

6. The composition of claim 5 wherein the concentration of the second active agent is about 62.5 nanomolar to about 1000 nanomolar.

7. The composition of claim 1 wherein the concentration of PAC-1 is about 1 µM to about 5 µM.

8. The composition of claim 4 wherein the concentration of PAC-1 is about 1 µM to about 5 µM.

9. The composition of claim 6 wherein the concentration of PAC-1 is about 1 µM to about 5 µM.

10. The composition of claim 1 wherein the composition comprises water, a buffer, a sugar, a cellulose, a cyclodextrin, dimethyl sulfoxide, polyethylene glycol, tocopherol, a liposome, a micelle, a binder, a lubricant, a sorbent, a vehicle, a disintegrant, a preservative, or a combination thereof.

11. A method of inhibiting the growth or proliferation of melanoma cancer cells comprising contacting the cancer cells with an effective amount of the composition according to claim 1, thereby inhibiting the growth or proliferation of the cancer cells; or
a method of inducing apoptosis in a melanoma cancer cell comprising contacting the cancer cell with an effective amount of the composition according to claim 1, wherein apoptosis is thereby induced in the cancer cell.

12. A method of treating melanoma comprising administering to a patient in need thereof, concurrently or sequentially, a therapeutically effective amount of the compound PAC-1 and a therapeutically effective amount of a second active agent, wherein the second active agent is an inhibitor of C-ros oncogene 1 (ROS1), anaplastic lymphoma kinase (ALK), tropomyosin receptor kinase A (TrkA), tropomyosin receptor kinase B (TrkB), and tropomyosin receptor kinase C (TrkC), the PAC-1 and the second active agent treat the melanoma synergistically at the dosage levels administered, and the melanoma is thereby treated.

13. The method of claim 12 wherein the melanoma is uveal melanoma or cutaneous melanoma.

14. The method of claim 13 wherein the uveal melanoma is a GNAQ mutant, a GNA11 mutant, a GNAQ wild type, or a GNA11 wild type, uveal melanoma.

15. The method of claim 12 wherein a resistance to treatment of the melanoma in the patient in need thereof is reduced, delayed, or eliminated or a metastasis of the melanoma in the patient in need thereof is reduced, delayed, or eliminated.

16. The method of claim 12 wherein PAC-1 synergizes with the second active agent in vivo, wherein:
the concentration of PAC-1 is about 1 uM to about 5 uM, and the concentration of the second active agent is about 62.5 nM to about 10,000 nM.

17. The method of claim 12 wherein the compound PAC-1 and the second active agent are concurrently administered to the patient.

18. The method of claim 12 wherein the compound PAC-1 and the second active agent are sequentially administered to the patient.

19. The method of claim 16 wherein the second active agent is entrectinib.

20. A method of treating uveal melanoma comprising administering to a patient in need thereof, concurrently or sequentially, PAC-1 and entrectinib, wherein the PAC-1 and entrectinib are administered at dosage levels that provide a synergistic melanoma treatment effect, compared to the administration of PAC-1 or entrectinib alone, and the uveal melanoma is thereby treated.

21. A method of treating cutaneous melanoma comprising administering to a patient in need thereof, concurrently or sequentially, PAC-1 and entrectinib, wherein the PAC-1 and entrectinib are administered at dosage levels that provide a synergistic melanoma treatment effect, compared to the administration of PAC-1 or entrectinib alone, and the cutaneous melanoma is thereby treated.

* * * * *